United States Patent [19]
Fortune et al.

[11] Patent Number: 5,141,513
[45] Date of Patent: Aug. 25, 1992

[54] SURGICAL TEMPLATE

[76] Inventors: John Fortune, 615 Osborne, West Covina, Calif. 91790; James Alexander, 1720 Mission #7, S. Pasadena, Calif. 91030

[21] Appl. No.: 519,374

[22] Filed: May 4, 1990

[51] Int. Cl.$^5$ ............................................. A61F 504
[52] U.S. Cl. ......................................... 606/96; 606/53
[58] Field of Search ............... 606/53, 96, 97, 98, 606/102, 130

[56] References Cited

U.S. PATENT DOCUMENTS

| | | | |
|---|---|---|---|
| 4,037,592 | 7/1977 | Kronner | 606/97 |
| 4,325,373 | 4/1982 | Slivenko et al. | 606/96 |
| 4,349,017 | 9/1982 | Sayegh | 606/96 X |
| 4,360,012 | 11/1982 | McHarrie et al. | 606/96 X |
| 4,457,307 | 7/1984 | Stillwell | 606/53 X |
| 4,483,344 | 11/1984 | Atkov et al. | 606/130 X |
| 4,703,751 | 11/1987 | Pohl | 606/53 X |
| 4,846,173 | 7/1989 | Davidson | 606/130 |
| 4,907,577 | 3/1990 | Wu | 606/96 X |

FOREIGN PATENT DOCUMENTS 664403 6/1963 Canada ............................. 606/130

OTHER PUBLICATIONS

*Operative Orthopedics*, vol. 1, Chap. 33 by Michael W. Chapman, M.D.
*Manual of Internal Fixation*, Second Edition, 1979, pp. 98–101, by Müller et al.

Primary Examiner—Robert A. Hafer
Assistant Examiner—Sam Rimell
Attorney, Agent, or Firm—Douglas A. Chaikin

[57] ABSTRACT

Disclosed herein is a surgical template including a base having a plurality of openings, including first and second slots. The template further includes a plurality of guides for guiding placement pins. The guides include first and second primary guides which are slidably and removably connected to the base through the first and second slots, respectively. The base further includes a secondary guide removably connected to the base. Each of the primary and secondary guides sized and shaped to cause the placement pins to be parallel to one another when inserted into the guides.

14 Claims, 6 Drawing Sheets

5,141,513

SURGICAL TEMPLATE

BACKGROUND OF THE INVENTION

1. Field of the Invention

This invention relates to medical instruments and more particularly to medical instruments for use in surgery to repair fractured bones.

2. Previous Art

Guide pins are used in certain selected orthopaedic procedures to correctly position a surgical implant so that anatomic reduction at the fracture is achieved. Examples of such fractures include simple supracondylar femur fractures; supracondylar fractures with associated comminution of the distal shaft; fractures of the lateral condyle extending up into the shaft; posterior tangential fractures of one or both condyles; inter- and supracondylar fractures (T or Y fracture); the bicondylar fractures combined with a comminuted fracture of the distal femur; and bicondylar fractures combined with distal comminuted fracture of the femoral shaft. Fractures at the proximal end of the femur, in the trochanteric and neck region, also require the use of guide pins.

In each of the surgical procedures to repair supracondylar femur fractures, intra-articular "primary" guide pins are used to align a "secondary" guide with respect to the knee joint and pin which in turn is used to correctly position the surgical implant across the fracture site.

The traditional surgical method for aligning and positioning the secondary guide pin is by a "free-hand" technique. Inherent in this "free-hand" technique is the risk of inaccurate placement of the surgical implant. This may result in a non-anatomic reduction of the fracture and an incongruous joint surface.

More specifically, the currently accepted procedure is to place two primary guide pins adjacent to the distal and anterior surfaces of the distal femur within the knee joint capsule A secondary guide pin is driven into the lateral surface of the distal femur parallel to the two primary guide pins. The selected implant is placed parallel to the secondary guide pin and should therefore be parallel to the distal and anterior articular surface of the distal femur. A detailed explanation of the above procedure is found in *Manual of Internal Fixation Technique Recommended by the AO Group* at 98–101, (Springer-Verlag Second Edition 1979) and *Operative Orthopaedics* Vol. 1, Ch33, "Supracondylar and Articular Fractures of the Distal Femur" at 401–412 (J.B. Lippincott Co. 1988) which are specifically incorporated herein by reference.

The accuracy of the placement of a secondary guide pin is based solely upon the perceptual skills of the operating surgeon and the one or two assistants who may be present. If the depth perception of either the surgeon or his assistants is inaccurate, the surgical implant will be placed inaccurately. This will produce a malreduction of the fracture and mal-alignment of the knee joint itself. A patient so afflicted may develop early degenerative arthritis and may lose substantial joint mobility. For some time, there has been a need for a guide system to replace the "free-hand" technique. The guide system should aide the surgeon and his assistants in precise placement of the selected implant with respect to the two inter-articular guide pins. Ideally, such a guide pin system would be used to simply and consistently orient a surgical implant parallel to the knee joint in three dimensions.

SUMMARY OF THE INVENTION

It is an object of this invention to provide a template for use in repairing the distal end of a fractured femur.

It is a further object of this invention to provide a surgical template to assist in the precise location of surgical implants in the femur.

In accordance with the above objects and those that will be mentioned and will become apparent below, the surgical template in accordance with this invention includes:

a base having a plurality of openings including first and second slots; and guide means for guiding placement pins, the guide means include first and second primary guides which are slidably and removably connected to the base through the first and second slots, respectively, and a secondary guide removably connected to the base, each of the primary and secondary guides sized and shaped to cause the placement pins to be parallel to one another when inserted in the guides, whereby during surgical operations to repair fractures of the distal femur, placement pins can be properly positioned in a patient and with respect to one another.

An additional embodiment of the surgical template in accordance with this invention includes:

a base having a plurality of openings including first and second slots; and pin guide means for guiding placement pins, the guide means include first and second primary guides which are slidably and removably connected to the base through the first and second slots, respectively; and a seating chisel guide removably and rotatably connected to the base, the seating chisel guide including a central slot opening sized and shaped to accommodate a chisel and having two fixation pin openings adjacent either side of the slot, whereby during surgical operations to repair fractures of the distal femur, the seating chisel can be properly positioned in a patient and immobilized to prevent angulation or rotation of the seating chisel during implantation.

The second embodiment particularly is useful for surgical procedures requiring a seating chisel.

Still other embodiments, feature the base being made from radiolucent material, such as graphite to facilitate lateral viewing of the distal femur with the device in place.

As a result of using the instant invention less mistakes occur and therefore fewer x-rays are necessary. This limit the radiation exposure to the patient and the operating room personnel.

It is an advantage of this invention to provide a template that significantly decreases the number of mistakes in positioning implants in the femur.

It is an additional advantage of this invention to provide a template which reduces the amount of radiation exposure to patient and operating room personnel during surgical reconstruction of a fracture of the distal femur.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 2:
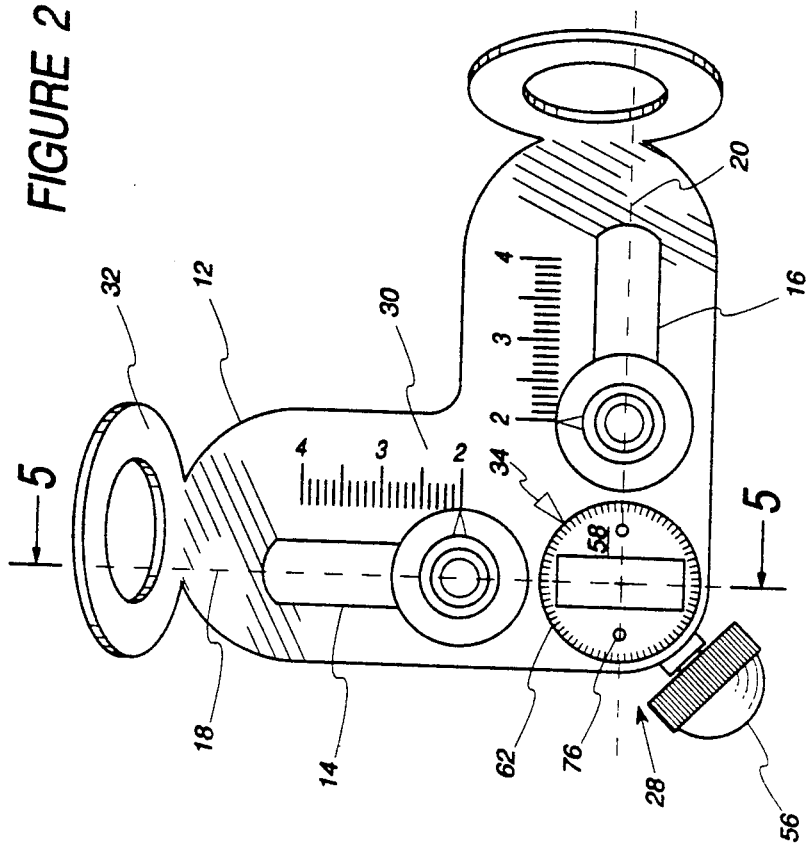
FIG. 2 is a top plan view of another embodiment of the surgical template of in accordance with this invention.
Figure 1:
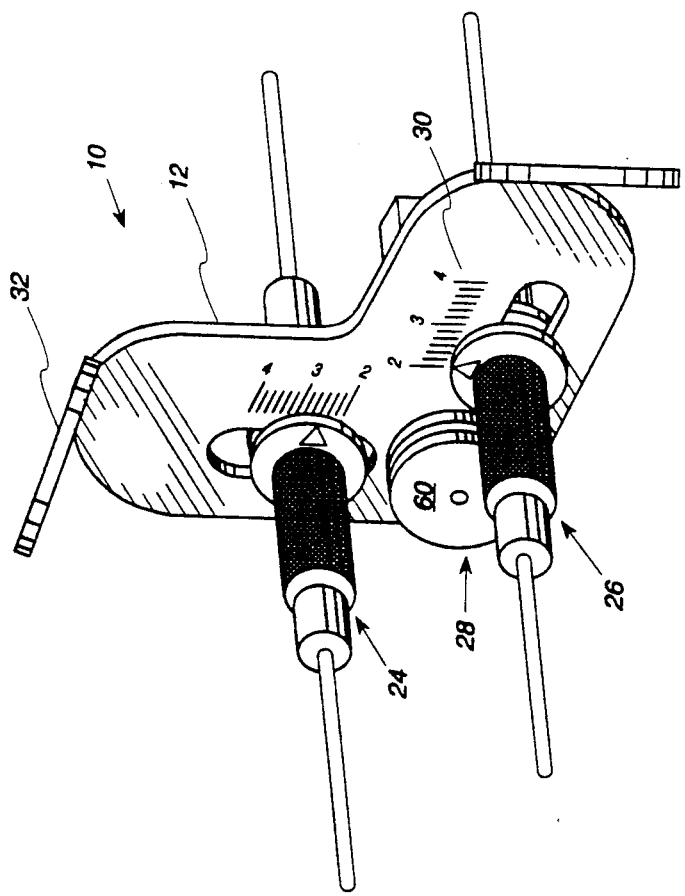
FIG. 1 is an elevated perspective view of surgical template in accordance with this invention.

The invention will now be described with respect to FIGS. 1-5 which illustrates the surgical template in accordance with the invention generally indicated by the numeral 10. The surgical template 10 defines a guide pin system for the placement of a secondary pin.

The surgical template 10 includes a base 12. The base is preferably 3 inches long and 3 inches wide. One of the preferred embodiment of the base 12 is made of stainless steel. Alternatively, the base 12 may be made of radiolucent material to allow x-rays and the like to pass through the base. Material such as graphite is suitable for this purpose.

The base 12 has a pair of openings defining first and second slots 14 and 16, respectively. Each slot is 3 cm long and each slot has a longitudinal centerline 18 and 20, respectively. The longitudinal centerlines 18 and 20 are perpendicular to one another and therefore intersect. At the intersection of the longitudinal centerlines 18, the base has a third opening 22.

The surgical template 10 includes primary and secondary guide assemblies. The primary guide assembly includes a first and a second primary guide assembly, 24 and 26, respectively, removably secured to the base 12 at slots 14 and 16, respectively. The primary guide assemblies 24 and 26 are each 2 inches long. A secondary guide assembly indicated generally by the numeral 28 is also removably secured to the base 12 at the third opening 22.

The base 12 includes reference scales 30 for assisting in accurately locating placement pins in a patient as will be more fully appreciated hereinafter. The reference scales 30 are used to determine the distance between the implant and the tibial femoral articulation. This assists the surgeon in correctly placing the device with respect to the knee joint.

The base 12 further includes gripping ears 32, which are used for gripping the surgical template 10 during a surgical procedure. The gripping ears 32 are circular with a center opening and angled to assist in gripping. The gripping ears 32 are used by the surgeon during the surgical procedure for holding on to the device.

A reference mark 34 is also included on the base 12 to assist in the accurate and consistent placement of a placement pin or a seating chisel guide. This will be more fully appreciated hereinafter with respect to the description of the surgical template 10 in use below.

As mentioned above, the primary guide assemblies 24 and 26 are removably secured to slots 14 and 16, respectively. As can best be seen in FIGS. 3 and 4, the primary guide assemblies 24 and 26 include a guide post 36 having a center opening extending from one end of the post 36 to the other for guiding a placement pin.

The primary guide assemblies 24 and 26 further have a proximal end 38 which is threaded and a distal end 40. The primary guide assemblies 24 and 26 include a stop ring 42 between the proximal end 38 and distal end 40. The stop ring 42 has a portion 44 which is shaped and sized to assist the primary guide assemblies 24 and 26 compatibly slide within the slots 14 and 16.

The primary guide assemblies 24 and 26 further include a locking ring 46 for removably securing the primary guide assemblies 24 and 26 to the base 12. The locking ring 46 has inside threads 48 (FIG. 5) which mate compatibly with the threads of proximal end 38. The locking ring 46 is tightened until the primary guide assemblies 24 and 26 are snugly secured to the base 12 in the selected position.

In order to assist in locating the primary guide assemblies 24 and 26 in the selected position, the primary guide assemblies 24 and 26 include a reference guide ring 50. The reference guide ring 50 is between the locking ring 46 and the stop ring 42 and serves as a washer for tightening the primary guide assemblies 24 and 26 in place on the base 12. The reference guide ring 50 has a reference mark 52 which is located on the reference guide ring 50 such that the mark 52 can be read with reference scales 30 as most clearly illustrated in FIGS. 1 & 2.

Figure 4:
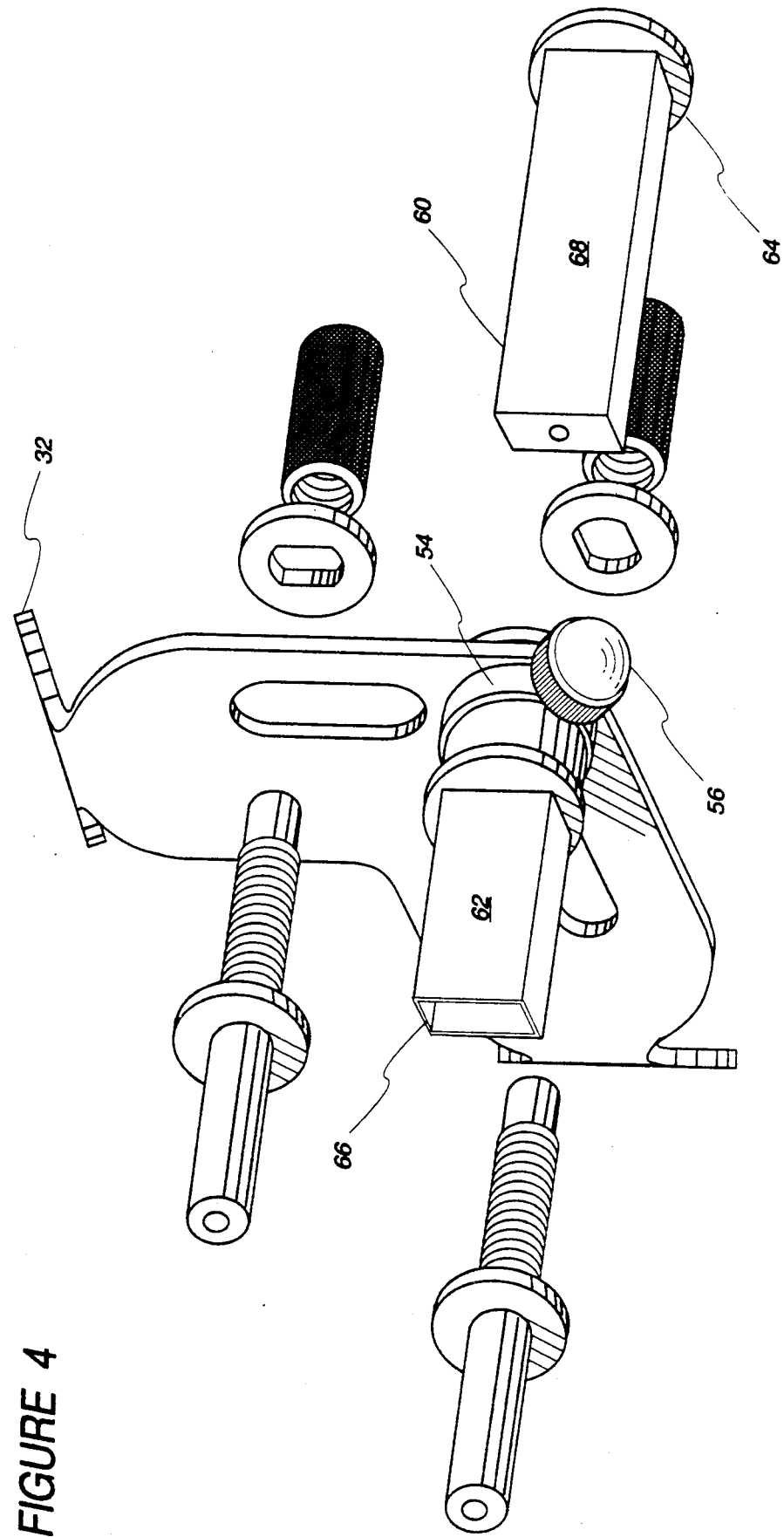
FIG. 4 is a rear exploded perspective view of the surgical apparatus of FIG. 3.
Figure 6:
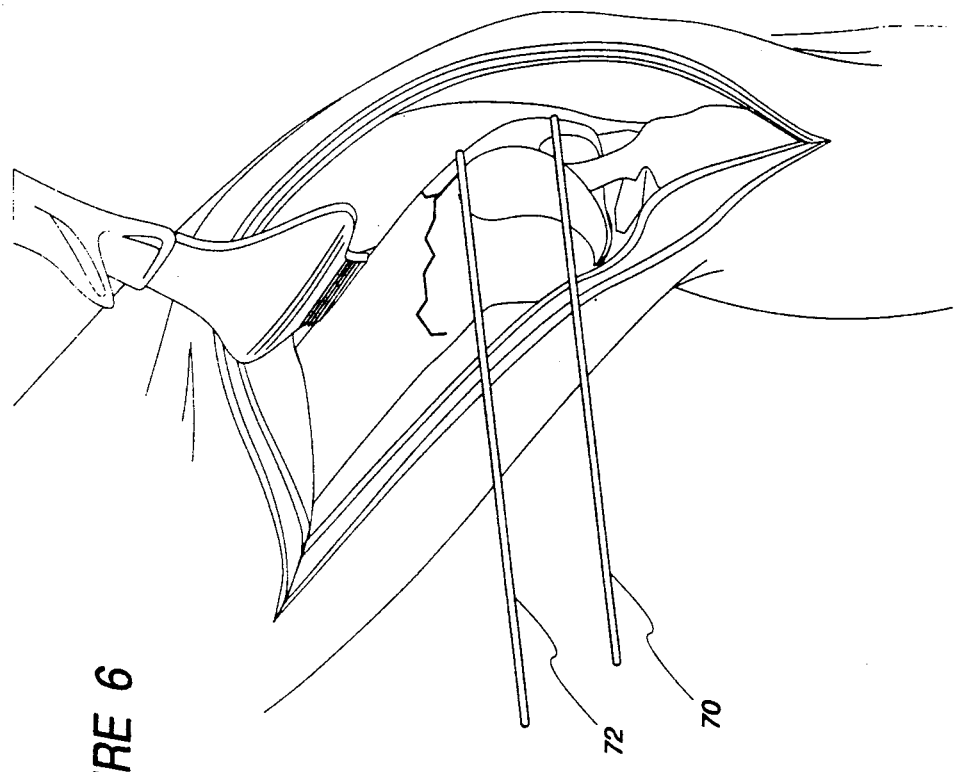
FIGS. 6-10 illustrate use of the surgical template in accordance with this invention showing use of both the secondary guide and the seating chisel.

The secondary guide assembly 28 includes a sleeve holder 54 which is removably secured to the base 12 by a locking screw 56, as best seen in FIGS. 2 and 4. The locking screw 56 includes a knurled knob for proper gripping and tightening. The sleeve holder 54 slidably and rotatably engages the base 12 at the third opening 22. The sleeve holder 54 can freely rotate and slide in the third opening 22 until locking screw 56 is tightened.

The sleeve holder 54 includes a front face 58 having references marks which are compatibly read with the reference mark 34. Again this allows the secondary guide assembly 28 to be accurately and consistently located in the patient.

Figure 5:
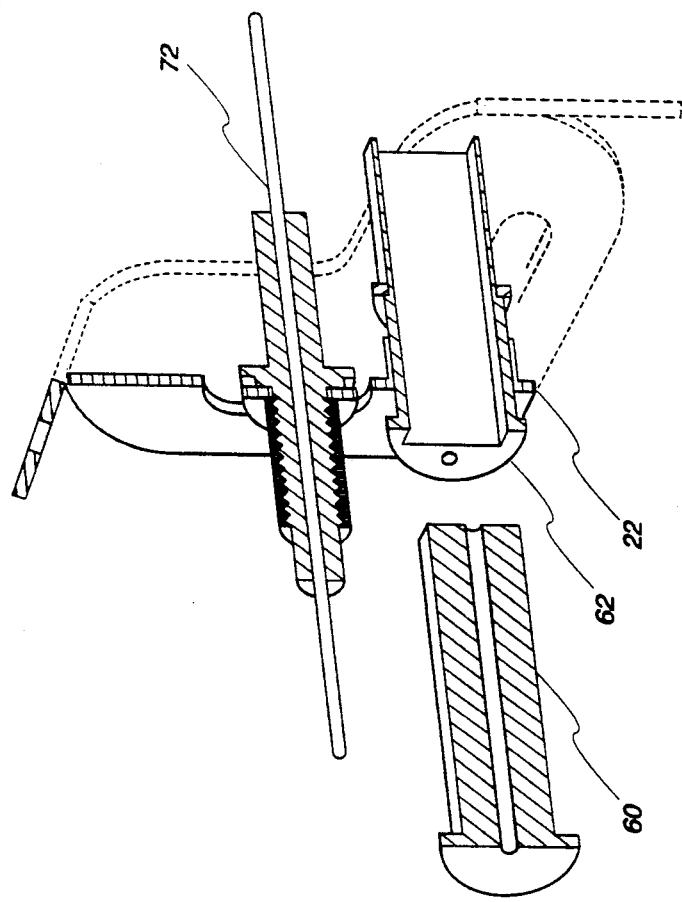
FIG. 5 is a cut away perspective view of surgical template of FIG. 2 illustrating use of the secondary guide.

The sleeve holder 54 accommodates either a distal femoral sliding screw guide 60' (FIGS. 1 & 3) or a seating chisel 62 (FIGS. 2, 4 & 5). With respect to the screw guide 60, the sleeve holder 54 is positioned as desired, the locking screw is tightened and the guide slidably engages the screw guide 60' as clearly illustrated in FIG. 3. The procedure is the same for seating chisel 62 as clearly illustrated in FIG. 3.

Each of the guides 60 and 62 are 2 inches high and have an outside diameter of $\frac{3}{4}$ inch. The sleeve holder 54 has an inside diameter of $\frac{3}{4}$ inch. And therefore, the guides 60 and 62 slide easily within the sleeve holder 54. The screw guide 60 includes a superficial cuff 64 which mates with front face 58.

Figure 3:
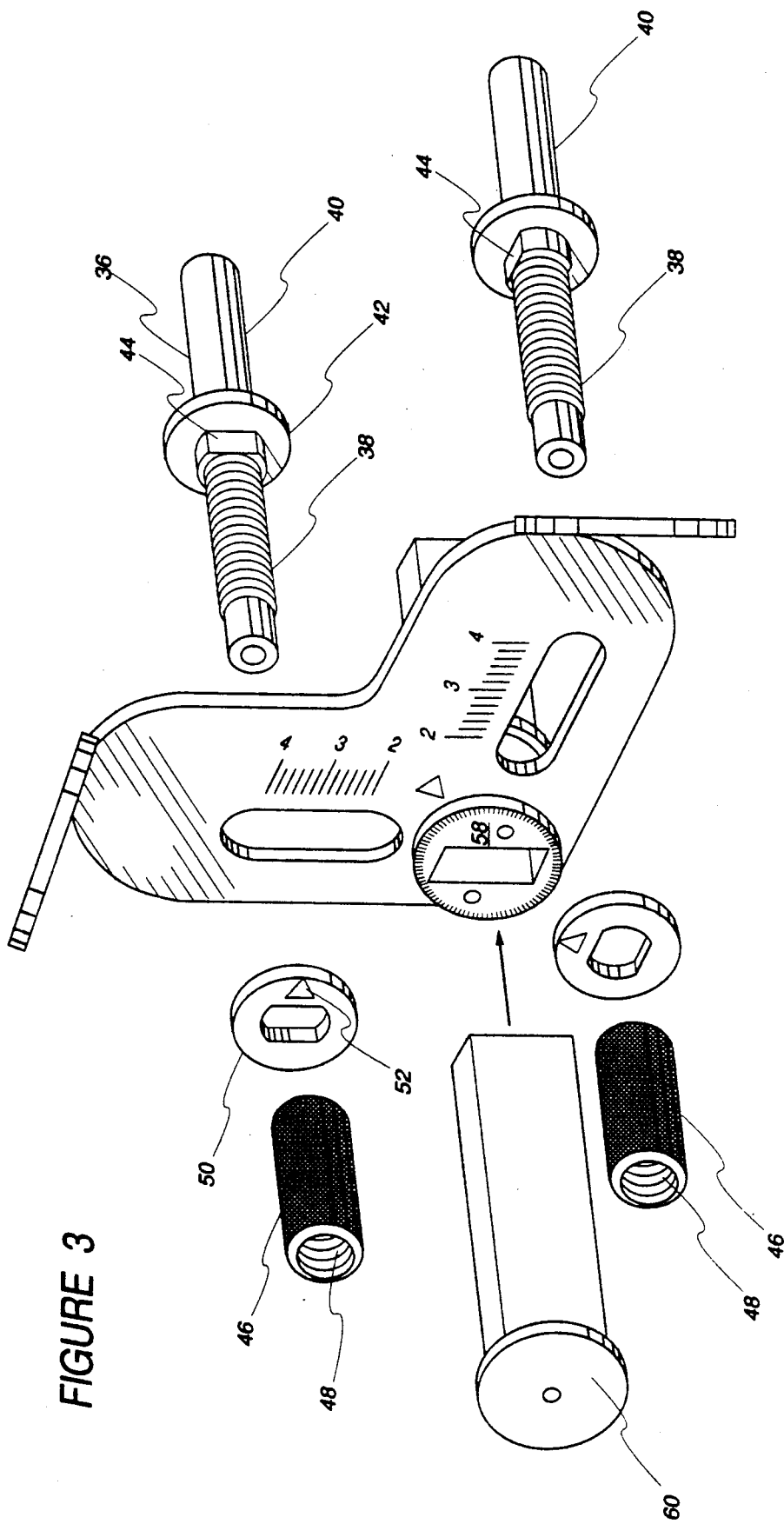
FIG. 3 is a front exploded perspective view of the surgical apparatus of FIG. 2 with the seating chisel adapter.

As shown in FIGS. 3-5, a modified screw guide 60' can be used in conjunction with the seating chisel guide 62. The seating chisel 62 has a central rectangular opening 66 for slidably engaging a seating chisel having rectangular portion 68 for same.

IN USE

The use of the surgical template 10 will now be described with reference to FIGS. 6-10 in which there is illustrated a supracondylar femur fracture.

A surgical incision is made into the patient locating a pair of tibio femoral and patello femoral placement pins 70 and 72. The tibia femoral placement pin 70 is located between the tibia and the femur. The patella femoral placement pin 72 is located between the patella and the femur.

The tibio femoral placement pin 70 is placed across the medial and lateral condyles and is inclined average of 97° from the axis of the femoral shaft. The patello femoral placement pin 72 is placed across the anterior aspect of the femoral condyle and is inclined approximately 5° to 10° from the axis of the posterior femoral condyles, which are parallel to the axis of the rotation of the knee joint.

Figure 8:
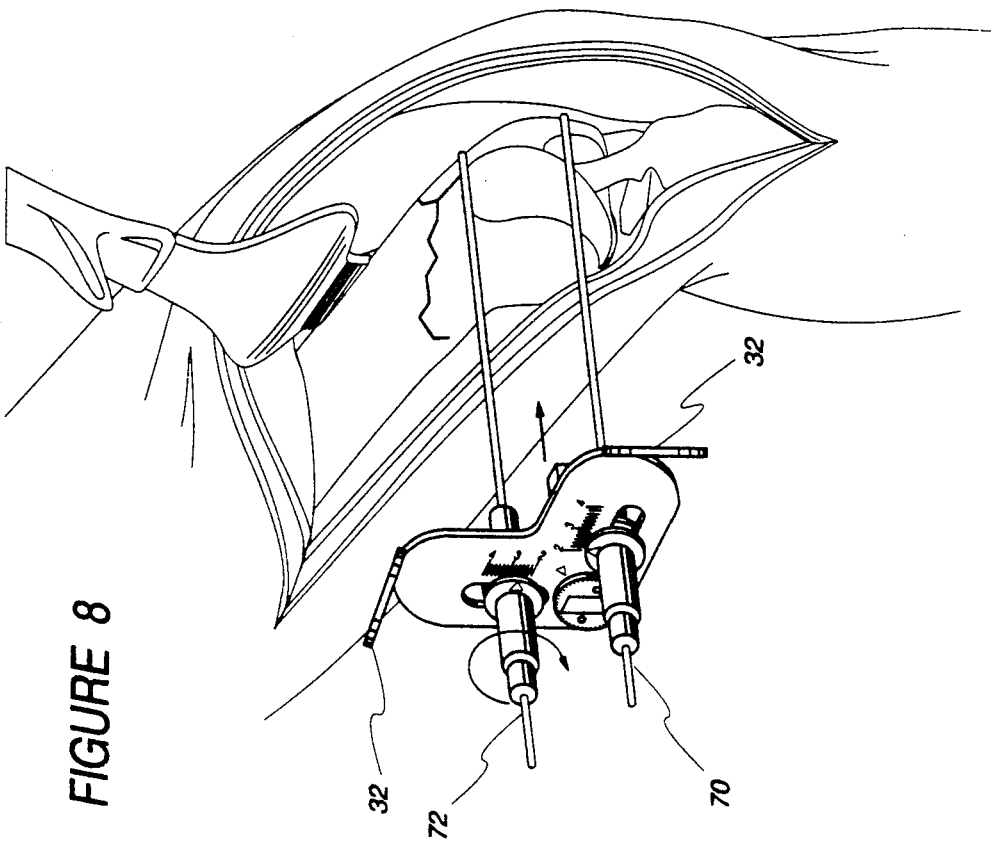
Figure 9:
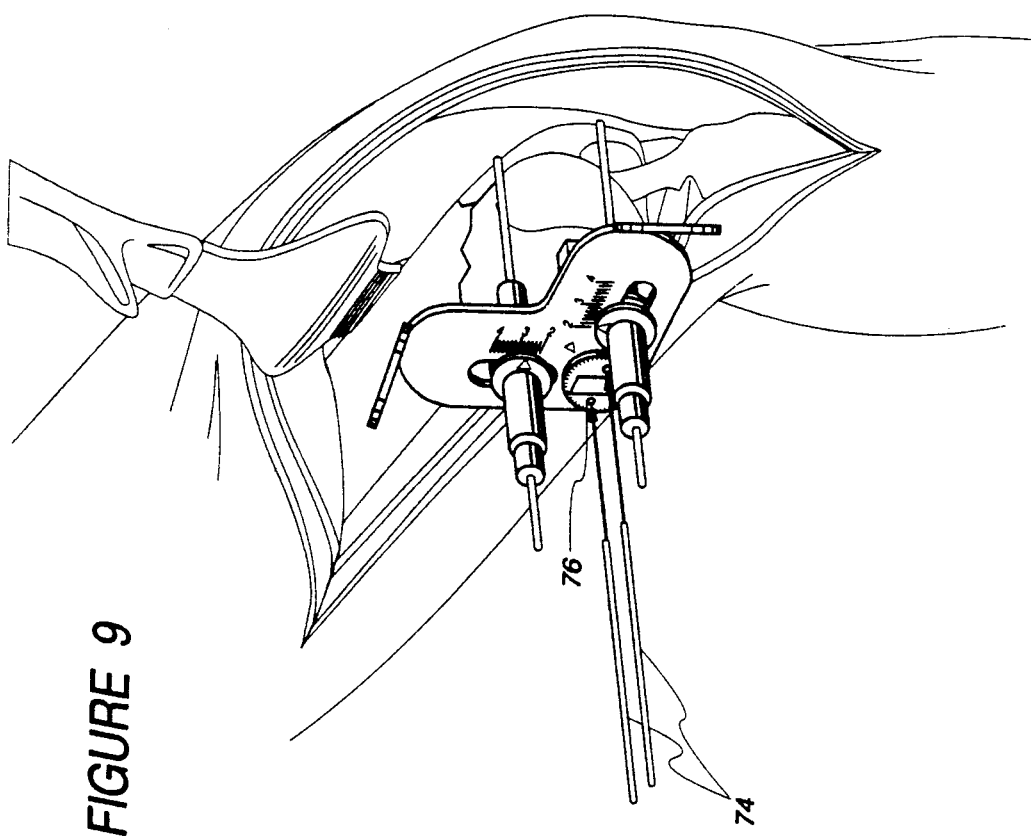

After the placement of the pins 70 and 72, the surgical template 10 is placed over the knee, guided into place by the placement pins 70 and 72 sliding engagement of the primary guide assemblies 24 and 26. After setting the reference mark 52 on the scales 30 for each of the primary guide assemblies 24 and 26 to the proper position, the locking rings 46 are tightened (FIGS. 8-9).

The secondary guide assembly 28 is set into position by tightening locking screw 56 firmly. Depending on the surgical procedure to be accomplished, secondary placement pins 74 can be inserted through a modified seating chisel guide 62 which has a pair of openings 76 extending through the seating chisel guide 62 as shown clearly in FIG. 9.

Figure 10:
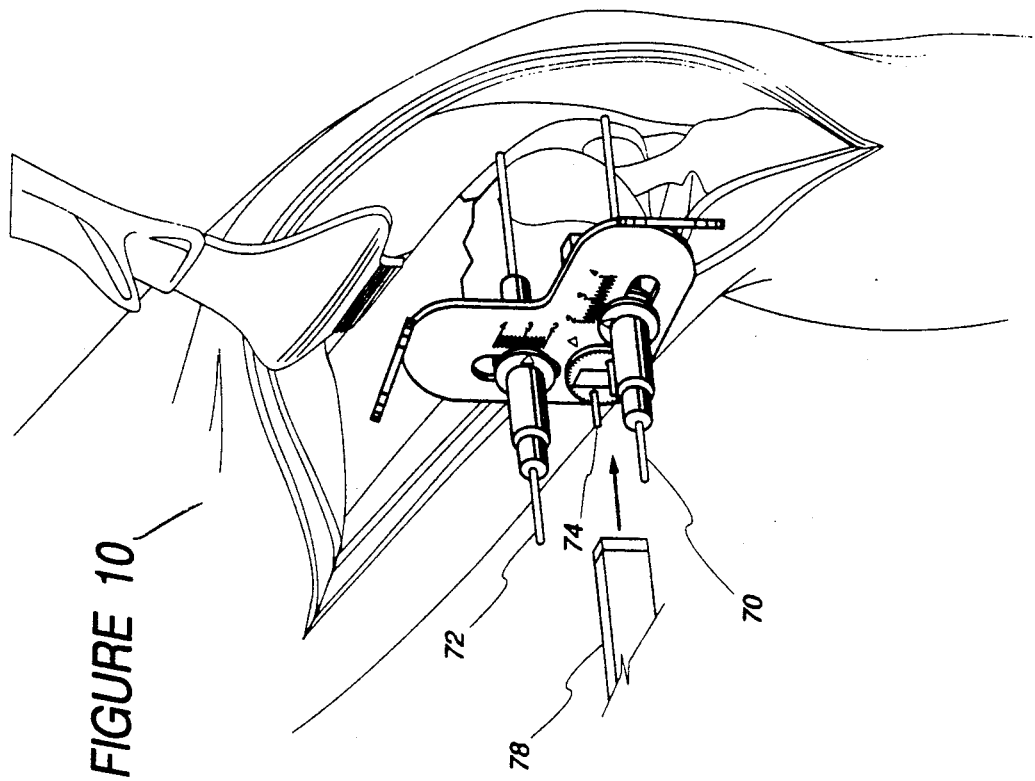

As shown in FIG. 10, a seating chisel 78 is now inserted into the seating chisel guide 62. It will be appreciated that the seating chisel 78 is inserted into the proper place without the aid of any surgery room assistants or by "eye-balling" and estimating the approximate location of the chisel. If the location is improper, the procedure must be done again and of course, this will be damaging to the patient.

Figure 7:
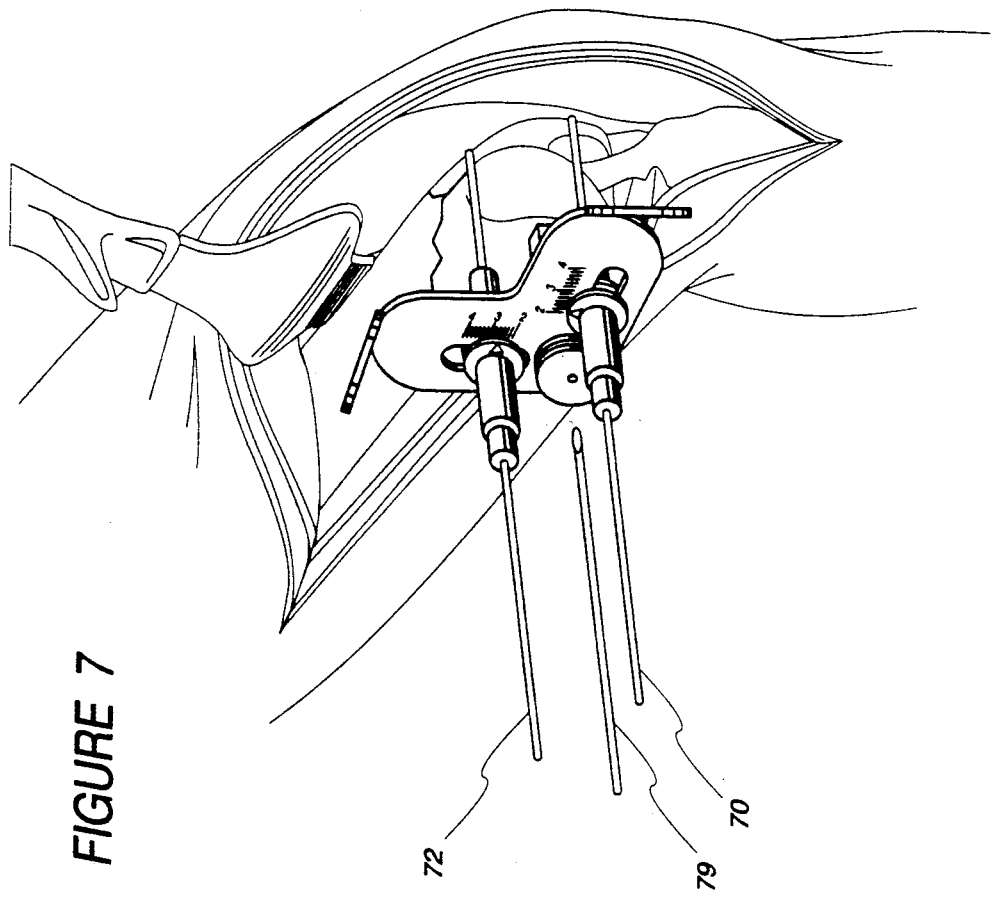

A similar procedure is used for inserting a secondary placement pin 79 for a distal femoral sliding screw FIG. 7. The prior art procedure required the use of at least one and usually two operating room personnel to properly place the screw.

After the placement pins and/or seating chisel are in correct position, the surgical implant is then set in place and the surgical procedure completed.

While the foregoing detailed description has described several embodiments of the surgical template in accordance with this invention, it is to be understood that the above description is illustrative only and not limiting of the disclosed invention. Particularly, the surgical template in accordance with this invention has been described with respect to just a few surgical procedures, it is comtemplated that the surgical template may be used in other surgical procedures not described above within the scope and spirit of this invention. Thus, the invention is to be limited only by the claims as set forth below.

What is claimed is:

1. A surgical template for use in surgical operations to repair a fracture of the distal femur, comprising:
    a base having a plurality of openings including first and second slots, the first and the second slots each have a longitudinal centerline, each of the longitudinal centerlines are perpendicular to each other;
    guide means for guiding placement pins, the guide means include first and second primary guides which are slidably and removably connected to the base through the first and second slots, respectively, and a secondary guide removably connected to the base, each of the primary and secondary guides sized and shaped to cause the placement pins to be parallel to one another when inserted in the guides,
    whereby during surgical operations to repair fractures of the distal femur, placement pins can be properly positioned in a patient and with respect to one another.

2. A surgical template as set forth in claim 1, wherein the opening for the secondary guide on the base is positioned at the intersection of the first and second centerlines.

3. A surgical template as set forth in claim 1, wherein the base is made from a radiolucent material for allowing x-rays to pass through the base.

4. A surgical template as set forth in claim 3, wherein the base is made from graphite.

5. A surgical template as set forth in claim 1, wherein adjacent each of the first and second slots there are reference scales.

6. A surgical template as set forth in claim 1, wherein base includes gripping ears for gripping the base during surgical procedures.

7. A surgical template as set forth in claim 5, wherein each of the guides includes a locking means for removably securing the guides to the base.

8. A surgical template as set forth in claim 7, wherein one end of the guide has threads and wherein the locking means is compatibly threaded therewith and wherein there a locking ring having an indicator compatible with the reference scale between the locking means and the guide such that as the guide is secured to the base the locking can be used as a reference with the scale.

9. A surgical template as set forth in claim 1, wherein the secondary guide is rotatable with respect to the base and wherein the secondary guide includes a locking means for securing the secondary guide to the base and for preventing rotation.

10. A surgical template as set forth in claim 1, wherein the guides are sized and shaped for fit with a distal femoral sliding screw.

11. A surgical template for use in surgical operations to repair a fractured knee, comprising:
    a base having a plurality of openings including first and second slots, the first and the second slots each have a longitudinal centerline, each of the longitudinal centerlines are perpendicular to each other; and
    pin guide means for guiding placement pins, the guide means include first and second primary guides which are slidably and removably connected to the base through the first and second slots, respectively; and
    a seating chisel guide removably and rotatably connected to the base, the seating chisel guide including a central slot opening sized and shaped to accommodate a chisel and having two fixation pin openings adjacent either side of the slot,
    whereby during surgical operations to repair fractures of the distal femur, the seating chisel can be properly positioned in a patient and immobilized to prevent angulation or rotation of the seating chisel during implantation.

12. A surgical template as set forth in claim 11, wherein the guide pins and the seating chisel are parallel to one another when the guide pins and chisel are inserted into the template through their respective guides.

13. A surgical template for use in surgical operation to repair fractures of the distal femur, comprising:
a base having plurality of openings including first and second slots, the first and the second slots each have a longitudinal centerline, each of the longitudinal centerlines are perpendicular to each other; and
pin guide means for guiding placement pins, the guide means includes first and second primary guides which are slidably and removably connected to the base through the first and second slots, respectively;
the base having a third opening for accepting a third guide which is removably and rotatably connected to the base, the third guide including a central slot opening sized and shaped for accommodating a seating chisel; and
an adapter sized and shaped for slidable engagement of the third guide central slot, the adapter including a central opening suitable for insertion of a placement pin,
whereby during surgical operations to repair fractures of the distal femur, the seating chisel can be properly positioned in a patient and immobilized to prevent angulation or rotation of the seating chisel during implantation.

14. A surgical template as set forth in claim 13, wherein the third guide defines a seating chisel guide sized and shaped to accommodate a chisel and the third guide having two guide pin openings adjacent either side of the slot.

* * * * *